United States Patent [19]

Gustafsson

[11] Patent Number: 5,044,586
[45] Date of Patent: Sep. 3, 1991

[54] MANIPULATOR FOR CRACK DETECTOR TRANSDUCERS

[75] Inventor: Bo Gustafsson, Västerås, Sweden

[73] Assignee: ASEA Brown Boveri AB, Västerås, Sweden

[21] Appl. No.: 500,512

[22] Filed: Mar. 28, 1990

[30] Foreign Application Priority Data

Mar. 29, 1989 [SE] Sweden .............................. 8901086
Dec. 14, 1989 [SE] Sweden .............................. 8904217

[51] Int. Cl.⁵ .............................................. G01N 29/04
[52] U.S. Cl. .................................... 248/124; 248/296; 73/618
[58] Field of Search ............... 248/124, 122, 125, 323, 248/324, 326, 327, 296; 73/618, 866.5

[56] References Cited

U.S. PATENT DOCUMENTS

| 4,018,082 | 4/1977 | Manoliu ............................ 73/618 X |
| 4,035,839 | 7/1977 | Eggleton et al. ..................... 73/618 |
| 4,326,694 | 4/1982 | Destree ............................... 248/676 |
| 4,943,020 | 7/1990 | Beaucoup et al. ................... 248/124 |

FOREIGN PATENT DOCUMENTS

| 1026479 | 3/1958 | Fed. Rep. of Germany ...... 248/324 |
| 163269 | 7/1988 | Japan .................................... 73/618 |

Primary Examiner—Alvin C. Chin-Shue
Attorney, Agent, or Firm—Watson, Cole, Grindle & Watson

[57] ABSTRACT

A manipulator for a transducer detector for indication of cracks and the like in hot metallic blanks, has the transducer driven relative to the blank by means of a car, a slide or other transducer carrier, which is placed inside or near a tube extending in the required scanning direction relative to the blank and being raisable and lowerable relative to the blank.

16 Claims, 4 Drawing Sheets

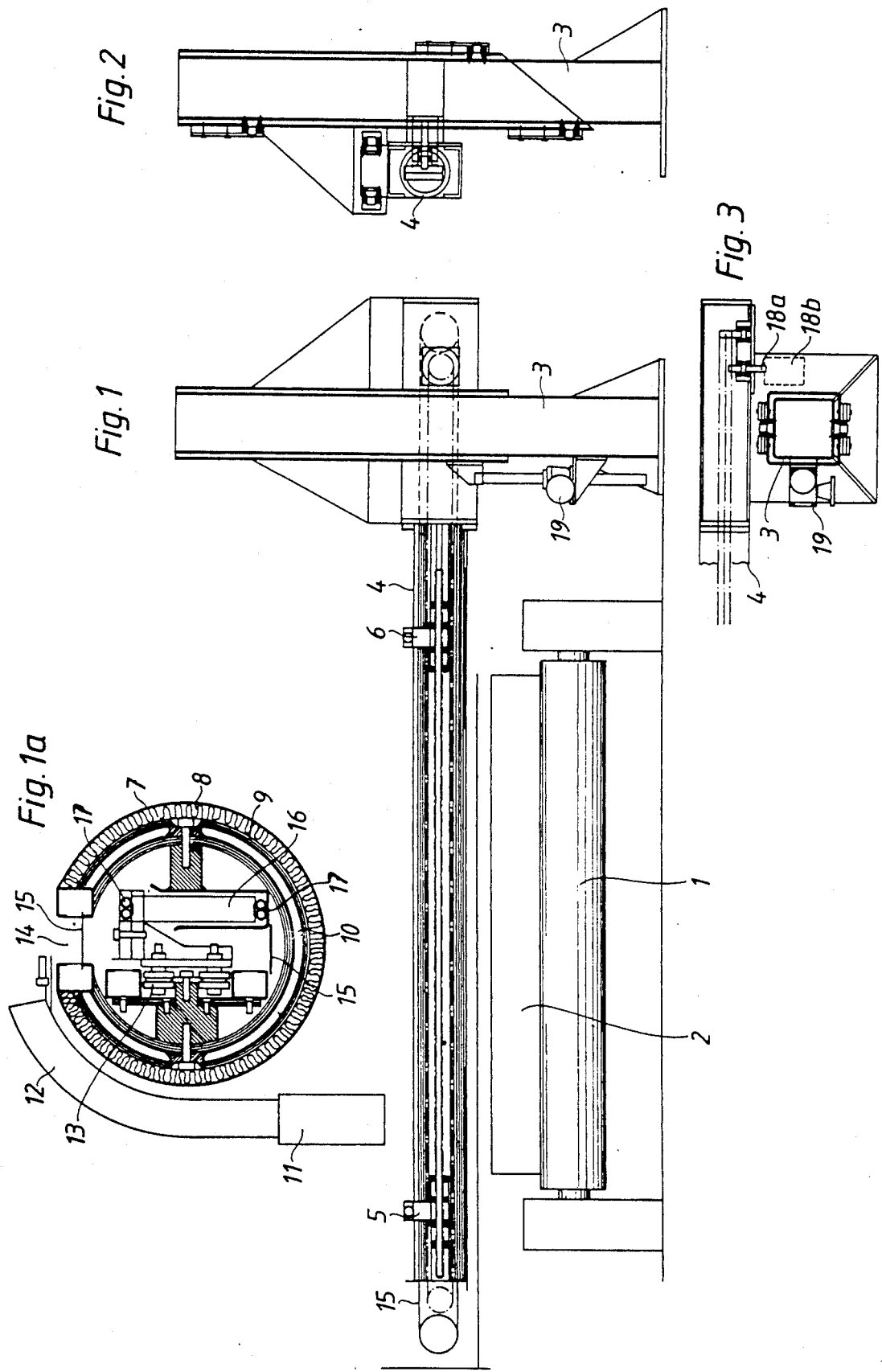

MANIPULATOR FOR CRACK DETECTOR TRANSDUCERS

TECHNICAL FIELD

The present invention relates to a transducer manipulator for transducer detectors for sensing the presence of inhomogeneities (e.g. cracks and the like) on test objects in the form of hot blanks, such as slabs, blooms, etc., the transducers being movable relative to the test object.

In crack indication of hot blanks, normally the greatest possible coverage by the transducer of the surface to be surveyed is aimed at, preferably a 100 per cent coverage.

BACKGROUND ART

Transducer manipulators for crack indication and the like on-line on hot blanks operate in a hostile environment and are therefore provided with extensive means for heat radiation protection, normally water-cooling. This results in a high weight for the movable structure used to support the transducer, with consequent problems in the response time of the transducer to tracking instructions.

A plurality of manipulator solutions are known, most of them based on one or more rotating, oscillating of self-oscillating transducers.

SUMMARY OF THE INVENTION

The present invention aims to provide a solution to the problems mentioned above and is characterized in that the transducer is driven across the blank by means of a car, a slide or other transducer carrier means, placed inside a tube which extends across or along the blank and which is raisable and lowerable relative to the blank. As examples of transducers that may be used in this connection may be mentioned the transducers disclosed in European Patent Application 0140895 published in the name of the assignee of this application.

By locating the movable transducer carrier in a raisable and lowerable tube and providing this with a slit, through which a supporting arm for the transducer is able to run, the movable weight can be kept low, and a safe environment can be provided for signal cables and the like, despite the fact that the transducer manipulator is located close to the hot surface of the test object.

The slit may be movable or a stationary slit can be sealed over regions not receiving the supporting arm of the transducer. The tube may be double-sheathed and water-cooled.

In a device according to the invention, high speeds and short turning distances (deceleration-stop-acceleration) may be imparted to the transducer. This leads to a good degree of coverage of the scanned surface and also leads to the use of transducers with small diameters of transducer coil.

The advantages of a device according to the invention are many. For example, less costly and less complicated manipulators, based on single coil scanning, may be used, which reduces the total price of detecting equipment, especially for equipment which is only intended to detect longitudinal cracks. The manipulator described is very well suited for detection on the upper side and the lower side of a hot blank. As blanks may be mentioned slabs, blooms and, possible, billets.

By virtue of the invention, the movable weight may be kept low, thus allowing shorter turning distances (e.g. about 20 cms) despite a high speed (e.g. 3 meters/second) above the surface of the blank. The blank may have been obtained by continuous casting and/or rolling and may be moved past the crack detector on a roller conveyor.

As a means of propulsion for the transducer may be used, for example, a chain-driven car or another alternative arrangement, such as a slide. Other means of propulsion, which in its entirety is placed inside a double-sheathed, water-cooled tube can be used. The tube, in turn, is normally provided with an outer efficient thermally insulating layer behind a thin heat-resistant sheet metal covering. Other embodiments of transverse tube may, of course, also be used. In this way the temperature changes, which arise between an instant when casting is in progress and an instant when casting is not in progress, are reduced. To prevent the penetration of dust or dirt into the space available for the propulsion device and the cable arrangement within the tube, the slit where the supporting arm or bracket of the transducer passes, may be covered with a sheet metal strip movably located in special low friction slots. The closed space thus created is connected to, for example, a compressed air network via a pressure reducing valve, whereby a limited overpressure can be created within the tube to prevent ingress of foreign bodies, hot gas, fumes, sparks and the like.

Between the movable and the fixed parts of the manipulator, signal transmission takes place by means of a flexible electrically conducting cable, preferably arranged to ensure a constant random capacitance between the conductors when rolling in and out the cable.

BRIEF DESCRIPTION OF THE DRAWINGS

The invention will now be further described, by way of example, with reference to the accompanying drawings, wherein:

FIG. 1 shows a first embodiment of manipulator device according to the invention seen from the side, FIG. 1a shows, on an enlarged scale, a cross-section of the tube of the device of FIG. 1, FIG. 2 shows the device of FIG. 1 in cross-section and from one end, FIG. 3 shows the end post of the device of FIG. 1 seen from above.

DESCRIPTION OF THE PREFERRED EMBODIMENTS

Figure 5:
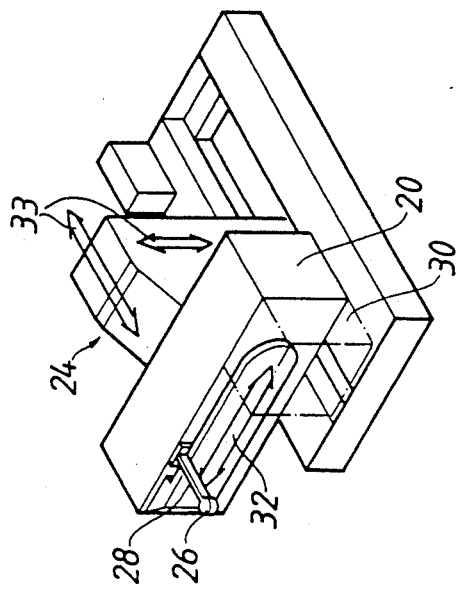
FIG. 5 shows a perspective view of one end of the device of FIG. 4.

FIG. 1 shows a roller conveyor 1 with a continuously cast or rolled metallic blank 2, which is hot and is to pass through a crack-sensing transducer arrangement. To one side of the roller conveyor 1 there is placed a supporting leg 3, which horizontally supports a transverse tube 4 which is raisable and lowerable by means 19 mounted on the supporting leg 3. FIG. 1 shows two positions 5, 6 for the crack-sensing transducer detector of the arrangement, which may be of the kind exemplified above. FIG. 1a shows details of this arrangement. It shows a double-walled tube with an outer heat-resistant plate 7. Inside the plate 7 there is arranged a thermally insulating layer 8 and inside of this, a double-sheathed cooled tube 9 through which cooling water circulates in channels 10. The transducer is shown at 11 in FIG. 1a and is arranged to be close to the upper surface of the hot blank 2. By means of a supporting arm (tube and/or cable) 12 the transducer 11 is connected to a car or other carrier means 13, placed inside the double-walled cooled tube 9. The supporting arm 12 passes through a slit 14 in the tube 9, which slit faces away from the hot blank 2. The car 13 is movable along the double-walled cooled tube 9 and is thus, because of its location inside the tube 9, protected against heat radiation from the blank 2. This makes it possible to construct the carrier means with a very low weight. The slit 14 can be supplemented with a protective strip 15, which is intended to prevent the penetration of dirt and the like into the space within the tube which contains the car 13 and signal devices. From the transducer 11 a flexible electrically conducting strip or cable 16 and a cooling water hose 17 extend to connection points within the tube 9. The covering strip 15 may be designed to be movable with the carrier means 13, for example the strip can be in the form of an endless belt (see FIG. 1) which accompanies the transducer 11 during its movements and is supported in low friction packings (not shown). The entire arrangement according to FIG. 1a may be rotated through 180° so that it is supported below the blank 2 and is thus able to monitor the under side of the blank 2, for example between two rollers of the conveyor 1. The transducer 11 is adapted to pass across the blank 2 at great speed so as to obtain a short traverse pitch over the surface of the blank 2 despite the high longitudinal speed of the latter. The surface of the blank 2 is thus scanned in the shape of a zigzag pattern.

FIG. 3 shows the supporting leg 3 seen from above and shows a shaft pin 18a (suitably positioned at an angle of 90° to the tube 4) which is jointed to a driving motor 18b. The double-sheathed supporting tube 4 is shown in end view in FIG. 2.

Where the drive equipment for the carrier means 13 comprises an electric motor/gear box/gear wheel, this is preferably located at one end of the tube and rotated 90° in relation to the tube 4 as shown in FIG. 3. The tube 4 with its drive equipment 18a, 18b can be applied to the supporting leg 3 via a raisable and lowerable bracket, the lifting machinery 19 of which is adapted such that the following functions can be performed, namely:

1. Adjustment of the transducer arrangement to accommodate different blank thickness,
2. Adjustment of the working range of the transducer across the blank,
3. Access to the rear end of the tube for electrical and coolant connections, and
4. Safety device for emergency lifting situations.

The carrier means 13 may be a general carrier of a wide range of different transducer types, and thus not just the ones exemplified above. As mentioned above, the transducer may be placed under the strand 2 for scanning the underside thereof. Different propulsion arrangements can be used, and by adjustment of the length of stroke and the shuttle frequency, manipulator equipment of the same basic design can be used for other types of blanks than slabs, for example for blooms. Also billets can be used as the test object by adaptation and optimization of the driving mechanism with respect to the smaller size of object being scanned.

As an alternative design it may be mentioned that the slit 14 in the transverse tube 4 may be covered with a ceramic layer (shown purely schematically by chain line 30 in FIG. 5), the transducer being placed behind this ceramic layer inside the tube. Such a ceramic layer may suitably be cooled by liquid or gas flows. The slit 14 covered with a ceramic layer must, of course, face the hot surface of the blank which is to be surveyed for defects.

Another alternative is to place a height adjustment device for the transducer 11 on the carrier means 13, in which case the entire facility for adjusting the working range of the transducer from the test object can be limited to the transducer 11 and/or its supporting arm 12.

A detector transducer which only moves along the edge of a test object, such as a blank, is an important commercial device and is less sensitive to where the transducer coil is located in relation to the edge of the test object.

As in the carrier arm design described above, the tube 9 can be provided with a slit in which the carrier arm for the transducer is able to run and the movable weight of the carrier means can be kept low. In addition, a good environment can be created for signal cables and electronic equipment within the tube, despite the fact that the transducer is always placed near the hot strand. Also in this case, the slit may be movable or sealed, and the tube may be double-sheathed and water-cooled. However, it would also be possible to use a design in which, instead of double sheathing, tube cooling is arranged by means of welded-on channels.

The transducer should be made movable along a predetermined path, for example along the space between two end rollers of an endless conveyor. The path length may be, for example, about 0.8 m. the limitation is due to scanning being performed on the lower side of the blank as well.

In a device according to this alternative embodiment, high speeds and short turning distances (deceleration-stop-acceleration) may be imparted to the transducer, which results in a good degree of coverage of the scanned surface even though the coil in the transducer has small dimensions.

In addition to the extra advantages derived by using a device according to this alternative, the advantages are also substantially the same as those with a device according to FIGS. 1 to 3. It may be mentioned that less costly and less complicated manipulators, based on single coil scanning, can be used, which reduces the total price of detection equipment, in particular for equipment which is only intended to detect longitudinal cracks. The described manipulator is excellently well suited for detection on the upper side and the lower side of a hot blank. As examples of blanks may be mentioned slabs, blooms and possibly also billets. Accordingly, the movable mass can be kept low in order thus to allow short turning distances (e.g. about 2 dm) despite a high speed (e.g. 3 m/s) above the blank surface. The blank may have been obtained by continuous casting and/or rolling and may have passed through the detector on a conveyor roller.

In a further preferred embodiment of the invention, the transducer is placed on a carrier arm, for example an angled arm, mounted on a turning device for turning this arm, for example through 180°, for scanning the lower side or, alternatively, the upper side of the blank. The turning device is suitably mounted on a carriage inside the tube or a guide at the tube. The same transducer can be used, after a simple turning movement, for scanning the upper and lower sides, respectively, of the blank. In this way, one manipulator transducer may be used in place of two.

By locating the pivot center of the transducer on a level with the center of the blank, the transducer will rapidly adopt a suitable lift-off (LO) distance for a new measuring sequence when shifting between sensing the upper and the lower sides. The switching can be performed while the transducer of the other side is active, and the transducer which is to start operating stands by when the transducer which is to stop operating has completed the measuring. This results in a high total effective measuring time despite the use of several different transducers. The reciprocating movement may be limited, for example to the distance between two subsequent rollers in the roller conveyor, for example 0.8 m.

A further embodiment comprises adding an additional transducer detector (e.g. placed on the transducer arm and angled forwards towards the blank). The additional transducer can be used to scan the surface on the short side of the blank.

Certain components of the electronics system for the transducer manipulator are suitably accommodated inside the tube. Such a system can be used for two or more of the transducers by providing the system with switches.

The manipulator tube which is raisable and lowerable with a special lifting device can be placed on a plate, which in turn can be positioned very exactly in a direction facing, or facing away from, the edge of the blank to ensure accurate edge tracking.

Figure 4:
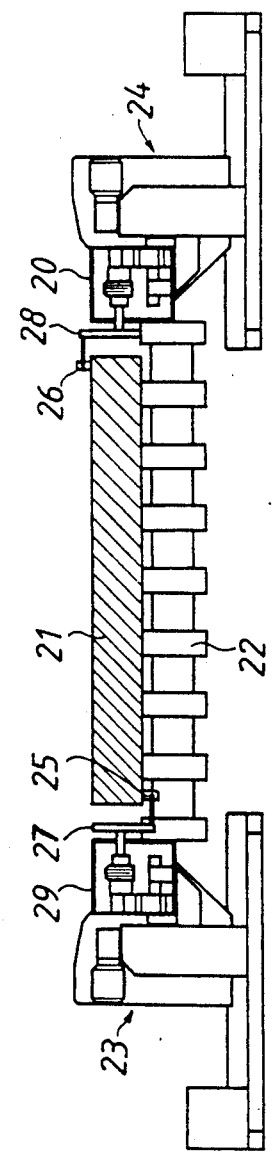
FIG. 4 shows a side elevation of an alternative embodiment of device.

FIG. 4 shows a blank 21 which is transported on a roller conveyor 22. At each side of the blank 21 there are transducer manipulators, one of which, 23, is adjusted for scanning the lower side and the other, 24, of which is arranged for scanning the upper side of the blank. The transducer manipulators 23, 24 are adapted to scan in paths along the blank 21, i.e. along its direction of transportation, and each transducer is rotatably switchable (180°) to alternatively scan the upper or the lower side of the blank 21. The actual transducer detectors are shown at 25 and 26. They are arranged at the end of rotatable arms 27, 28, which are rotatably journalled and mounted on transportable carriages in square section tubes 29, 20, or on guides in these tubes. The tube/tubes 29, 20 may, of course, have a different section, such as circular, and the arms 27, 28 can be moved along a slit in the tube which may be covered by means of a strip which is movable with the respective arm.

FIG. 5 shows a perspective view of the manipulator 24, the arrows 32 designating the transportation directions of the arm 28 and the two arrows 33 designating the adjustability of the manipulator towards and away from the blank 21 and upwards and downwards relative to the conveyor 22.

Figure 6:
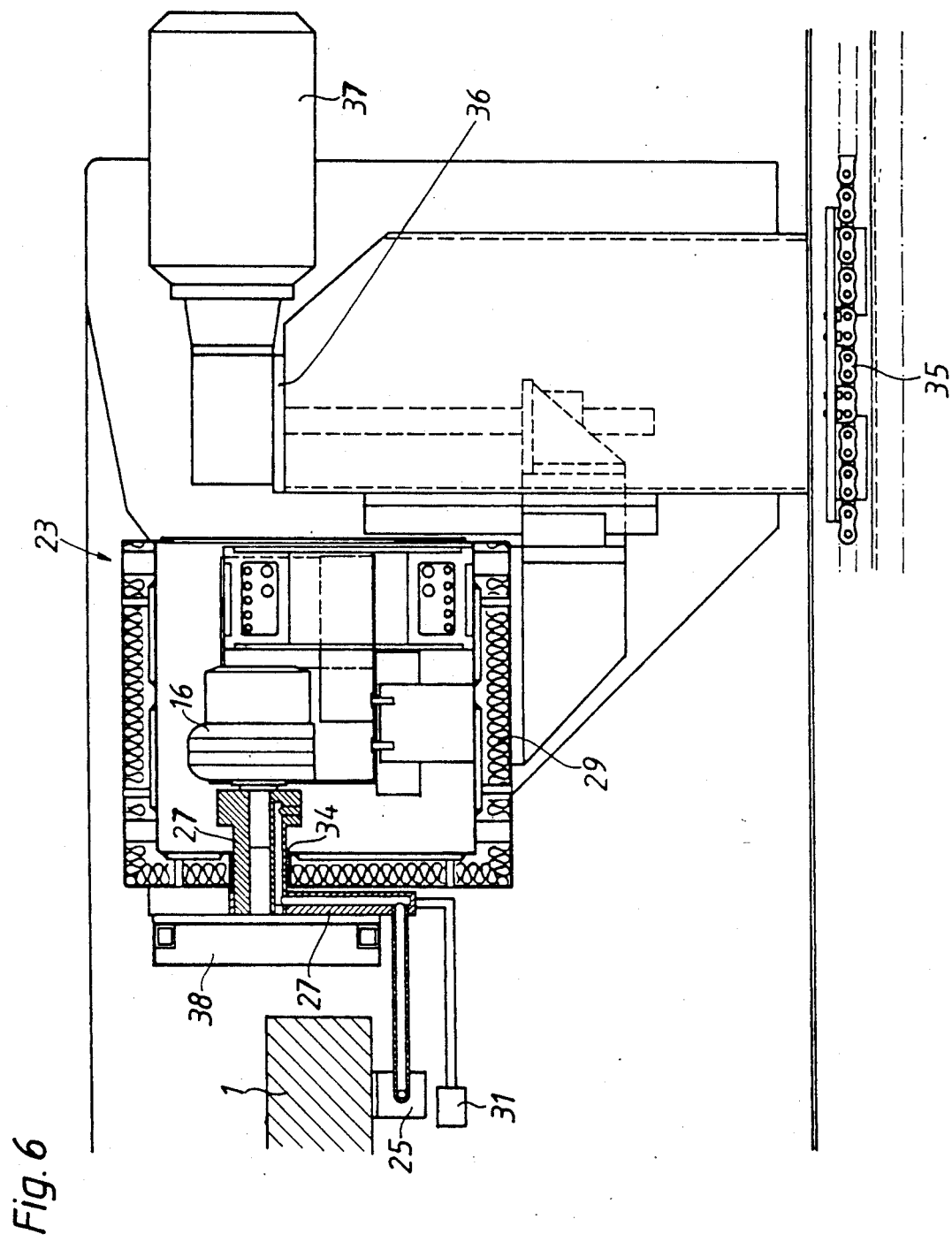
FIG. 6 shows part of the manipulator device of FIG. 4 in partial section and on an enlarged scale.

FIG. 6 shows in greater detail the manipulator 23.

The transducer detector 25 is placed at the end of a rotating arm 27, which is transportable in a slit 34 in the square section tube 29. The arm 27 is rotatably journalled inside the tube 29 and the transducer 25 can be rotated from a scanning position adjacent to the lower side of the blank 21 to a position adjacent to the upper side of the blank 21 and vice versa.

The numeral 31 designates a further transducer for scanning the side surface of the blank 21. The transducer 31 can be connected to the arm 27 as shown but it could be separated therefrom and have a separate entry point into the tube 29. To illustrate the possibility of enclosing the support arm and its sensing transducer behind a protective refractory, electrically transparent covering layer (e.g. of ceramic), FIG. 5 shows part of a protective cover 30 in chain lines at one end of the tube 20.

From FIG. 6 it can be seen that lateral transportation of the tube 29 with its transducers 25, 31 can be performed by means of a chain driven member 35. The turning device is shown at 36 and 37 designates an operating member (e.g. a motor). As can be seen, the tube 29 is heat-insulated. A water-cooled covering strip 38 can be used for covering the slit 34.

Figure 7:
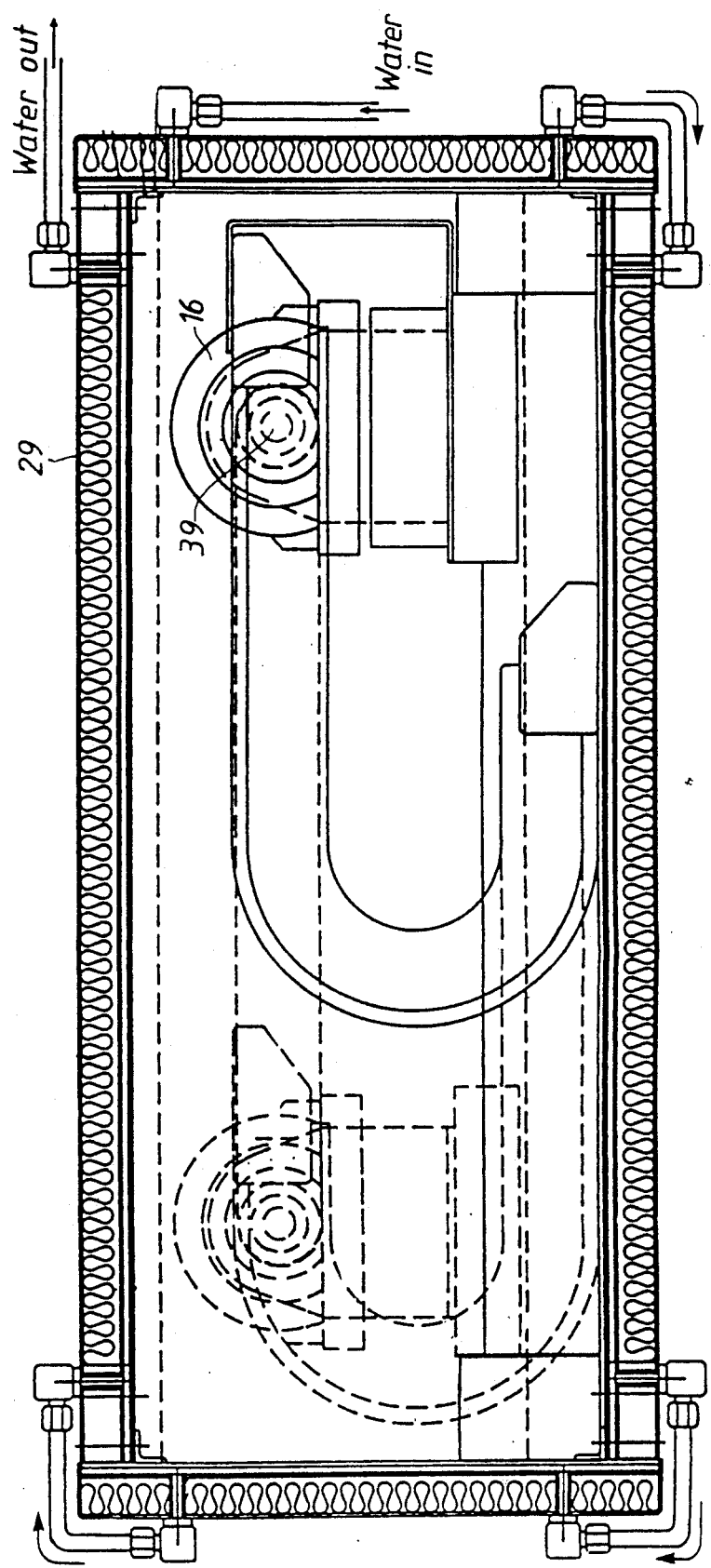
FIG. 7 shows a section of the device of FIG. 6 seen from the front.

FIG. 7 shows the tube 29 in longitudinal section with a carriage 39 for supporting the operating arm 27 with its transducer 25. The length of the tube indicates the length of the transportation path possible with this manipulator but this can clearly be varied as required.

The invention can be varied in many ways within the scope of the following claims.

I claim:

1. A transducer manipulator for supporting a transducer detector for movement over the surface of a hot test object for the indication of surface defects on the hot test object, comprising a transducer carrier for supporting said transducer detector, a tube for supporting said transducer carrier and extending across the surface of the test object, means for moving said tube towards and away from said test object, said transducer detector being mounted outside said tube and being connected to said transducer carrier by a supporting arm passing through a longitudinally extending slit in said tube, a thin strip covering said slit to prevent the penetration of foreign bodies into the interior of said tube.

2. A transducer manipulator acccording to claim 1, wherein the strip is movable with the transducer movements.

3. A transducer manipulator according to claim 1, wherein the tube extends transversely relative to the blank and is provided with means for water cooling the tube.

4. A transducer manipulator according to claim 3, wherein the tube is provided with at least one thermally insulating layer.

5. A transducer manipulator according to claim 1, wherein the length of movement of the transducer detector is adjustable.

6. A transducer manipulator according to claim 1, wherein the transducer, the carrier and the trannsversely extending tube are rotatable into a position, substantially 180° in relation to a previous position.

7. A transducer manipulator according to claim 1, wherein the transducer carrier includes a supporting arm mounted on a rotating device for rotating the supporting arm.

8. A transducer manipulator according to claim 11, wherein the rotating device is placed inside the tube.

9. A transducer manipulator according to claim 1, wherein the transducer movement is limited to a preset distance, for example between two end rollers of a roller conveyor.

10. A transducer manipulator according to claim 1, wherein an additional transducer is located at the carrier means for scanning a different side of the test object.

11. A transducer manipulator according to claim 1, further comprising a transducer with associated means is placed on the opposite side of the test object for scanning of the lower side and the upper side of the object.

12. A transducer manipulator according to claim 7, wherein the supporting arm consists of a two-part angled arm, the part of which is closest to the tube is rotated by means of a rotating device and the other part of which supports the transducer.

13. A transducer manipulator according to claim 1, further comprising means for moving the tube to and from the test object.

14. A transducer manipulator for supporting a transducer detector for movement over the surface of a hot test object for the indication of surface defects on the hot test object, comprising a transducer carrier for supporting said transducer detector, a tube for supporting said transducer carrier and extending across the surface of the test object, means for moving said tube towards and away from said test object, said transducer detector being mounted inside said tube and being connected to said transducer carrier by a supporting arm behind a longitudinally extending slit in said tube, a thin ceramic layer covering said slit to prevent the penetration of foreign bodies into the interior of said tube.

15. A transducer manipulator according to claim 14, wherein the ceramic layer is adapted to be cooled by liquid or gas.

16. A transducer manipulator for supporting a transducer detector for movement over the surface of a hot test object for the indication of surface defects on the hot test object, comprising a transducer carrier for supporting said transducer detector, a tube having a square section for supporting said transducer carrier and extending across the surface of the test object, said transducer carrier being movable inside said tube, means for moving said tube towards and away from said test object, means for water-cooling said tube, said transducer detector being mounted outside said tube and being connected to said transducer carrier by a supporting arm passing through a longitudinally extending slit in said tube, a thin strip covering said slit to prevent the penetration of foreign bodies into the interior of said tube.

* * * * *